United States Patent [19]

Generales, Jr.

[11] 4,166,452
[45] Sep. 4, 1979

[54] APPARATUS FOR TESTING HUMAN RESPONSES TO STIMULI

[76] Inventor: Constantine D. J. Generales, Jr., 115 Central Park West, New York, N.Y. 10023

[21] Appl. No.: 866,958

[22] Filed: Jan. 5, 1978

Related U.S. Application Data

[63] Continuation-in-part of Ser. No. 682,495, May 3, 1976, abandoned.

[51] Int. Cl.² .............................................. A61B 5/16
[52] U.S. Cl. .................................. 128/741; 35/22 R; 273/1 E; 128/745; 128/746
[58] Field of Search ............... 128/2 N, 2 S; 273/1 E; 35/22 R

[56] References Cited

U.S. PATENT DOCUMENTS

| | | | |
|---|---|---|---|
| 2,678,692 | 5/1954 | Ranseen | 128/2 N |
| 3,503,608 | 3/1970 | Ylinen | 273/1 E |
| 3,563,230 | 2/1971 | Gibbs et al. | 128/2 N |
| 3,698,385 | 10/1972 | Low et al. | 128/2 N |
| 3,869,812 | 3/1975 | Arakelian et al. | 35/22 R |
| 3,892,053 | 7/1975 | Booher | 35/22 R |

OTHER PUBLICATIONS

Houghton; D. et al., *Behav. Res. Meth. & Instru.*, 1973, vol. 5(3), pp. 273-276.

*Primary Examiner*—Kyle L. Howell
*Attorney, Agent, or Firm*—Peter K. Kontler

[57] ABSTRACT

The system of the invention includes provisions for administering a plurality of tests sequentially to a subject, with each test including a plurality of programmable visual, auditory and/or tactile stimuli and programmed desired responses. The system includes novel circuitry for interrelating the operation of the stimuli and the responses and determining premature, incorrect and correct responses and providing a printout of the reaction time of each response. The system also indicates a response which goes beyond a set maximum time period.

22 Claims, 18 Drawing Figures

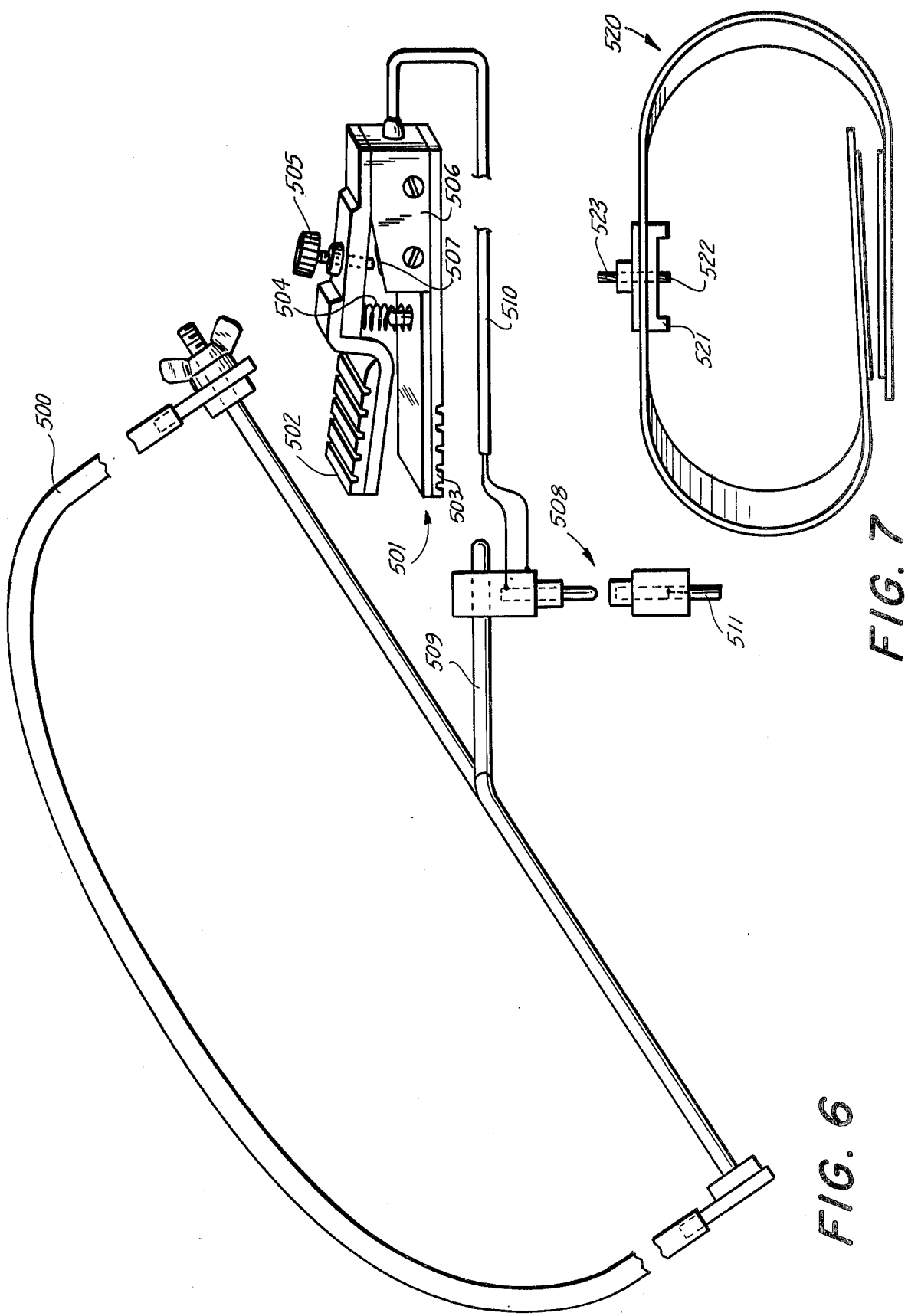

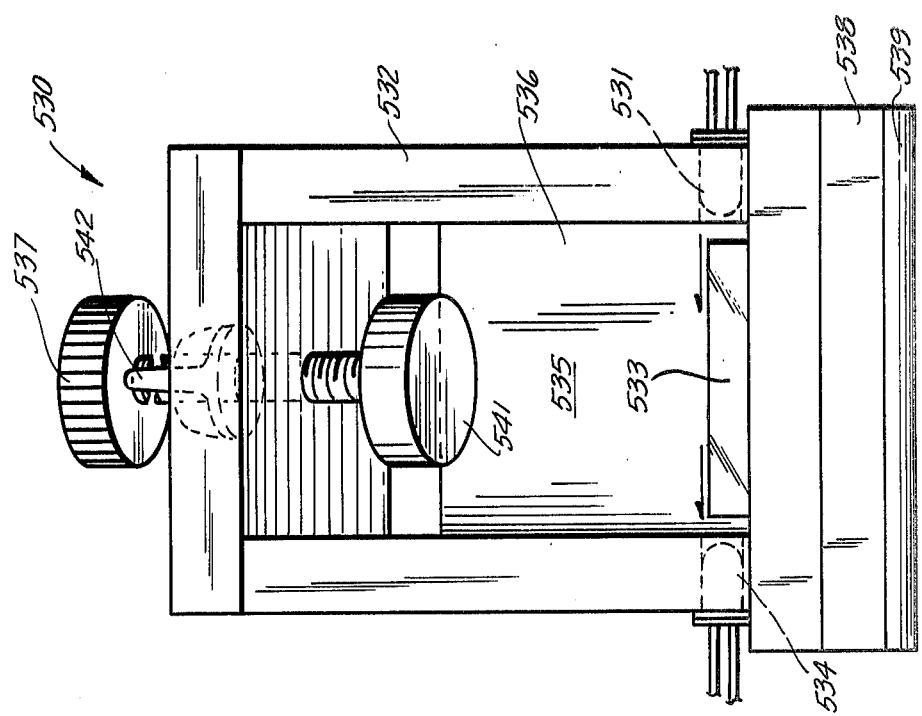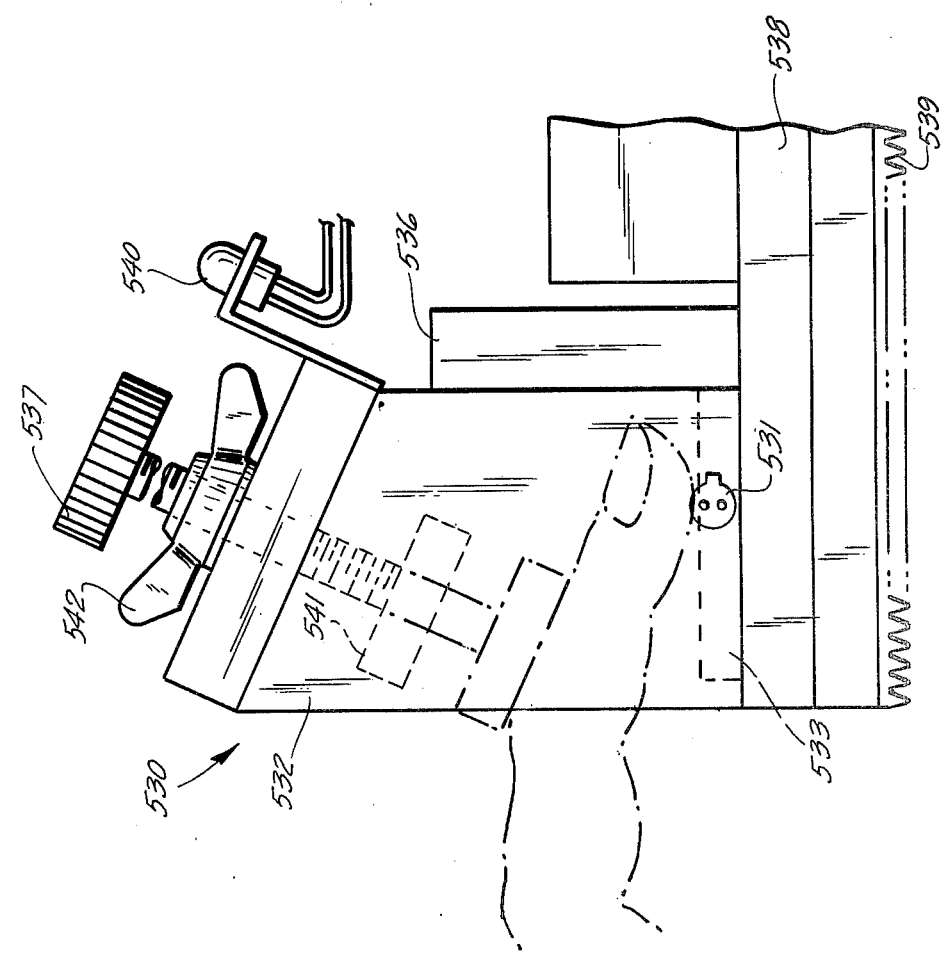

APPARATUS FOR TESTING HUMAN RESPONSES TO STIMULI

CROSS-REFERENCE TO RELATED APPLICATION

This is a continuation-in-part of my copending application Ser. No. 682,495 filed May 3, 1976 for "Apparatus for testing human responses to stimuli", now abandoned.

BACKGROUND OF THE INVENTION

Apparatus for testing subjects for response to stimuli are known in the prior art. Reference may be had to U.S. Pat. No. 2,678,692 to Ranseen or to U.S. Pat. No. 3,869,812 to Arakelian et al. However, none of presently known apparatus are able to provide such selection and programming of stimuli and desired response(s) as to be useful, both to the medical profession for diagnostic purposes and to other disciplines for less technical purposes.

OBJECTS AND SUMMARY OF THE INVENTION

An object of the invention is to provide a highly sensitive apparatus for measurement of conjugated visual, auditory and tactile responsiveness toward holistic evaluation of human cerebro-neural functions under physiological and other pathological conditions where great precision is required.

Another object of the invention is to provide the apparatus with novel and improved means which enables a subject to rapidly react to tactile stimuli in the form of electric shocks or the like.

A further object of the invention is to provide an apparatus which can be used by physicians, military and intelligence authorities, employment agencies, personnel departments of firms, educational and other institutions, police, judiciary and/or other agencies.

An additional object of the invention is to provide an apparatus whose versatility greatly exceeds the versatility of presently known apparatus for testing subjects for response to stimuli.

Another object of the invention is to provide an apparatus which can furnish immediate visible and/or audible indications of the results of tests as well as a permanent record of each test.

An ancillary object of the invention is to provide the apparatus with novel and improved means for the application of tactile stimuli to a subject and with novel and improved means for indicating the reaction of a subject to such stimuli.

A further object of the invention is to provide an apparatus of the above outlined character whose controls are sufficiently simple to enable a nurse or another paraprofessional to manipulate the apparatus during testing of subjects.

Another object of the invention is to provide the apparatus with novel and improved auxiliary equipment which insures that a subject can undergo a large number of tests within a relatively short interval of time and with a minimum of strain.

The improved apparatus comprises a plurality of stimuli including tactile stimuli, means for selecting and setting into program each of the plurality of stimuli, response means for operation by a subject under test including a device which is arranged to furnish indications as a result of relative movement of the jaws of a subject under test on application of a stimulus (especially a tactile stimulus), a clock which is coupled to the stimuli and to the response means to register the time which elapses after the start of a test and the operation of a stimulus for the subject to provide a response, and means for controlling and interrelating the operation of stimuli, response means and clock.

Of the five major physical senses, the olfactory (smell) and taste sensory systems—being qualitative and fickle by nature—are not amenable to reliable quantitative calibration. Furthermore, these two systems, in spite of safeguards and controls, are constantly affected by undesirable extraneous factors which defy attempts at their elimination. Therefore, the scientific method cannot be pursued technologically with accuracy.

There are 140 different biomedical combinations of the vital triple (tactile, auditory and visual) sensory speed tests including the right and left cerebral hemispheres and the innervations crossing over to the opposing neuro-muscular groups of the four extremities that govern flexor and extensor movements. Emphasis is on the holistic solution and integration.

The novel features which are considered as characteristic of the invention are set forth in particular in the appended claims. The improved apparatus itself, however, both as to its construction and its mode of operation, together with additional features and advantages thereof, will be best understood upon perusal of the following detailed description of certain specific embodiments with reference to the accompanying drawing.

BRIEF DESCRIPTION OF THE DRAWING

FIG. 6 is a perspective view of a device, and a halter therefor, which is actuatable by a subject in response to the application of tactile stimuli;

FIG. 7 is a perspective view of a device for the application of tactile stimuli;

FIG. 8 is a side elevational view of a subject response device which is actuatable by a portion of an extremity; and FIG. 9 is a front elevational view of the subject response device of FIG. 8.

DESCRIPTION OF THE PREFERRED EMBODIMENTS

Figure 1:
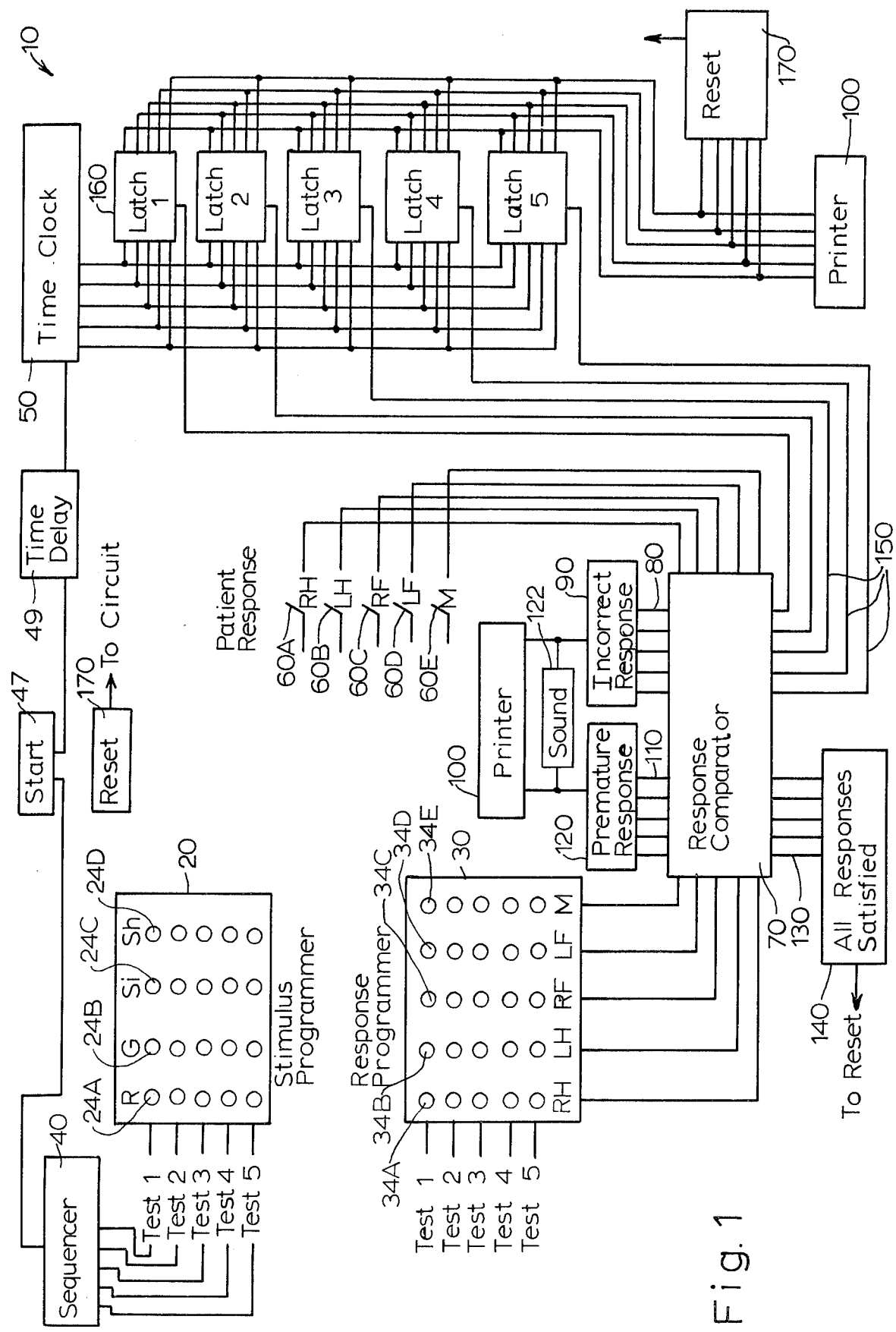
FIG. 1 is a schematic representation of a system embodying the invention.

The principles of the invention are illustrated with respect to the system 10 shown in block diagram in FIG. 1. In the system, block 20 includes rows and columns of circles, each of which represents a push-button switch 24. Each row of switches represents a test, five tests being shown, and the switches also represent the stimuli that can be programmed into each test. Each column of switches represents a particular stimulus; for example, the first column, under the letter R, includes switches 24A for energizing a red light stimulus; the second column, under the letter G, includes switches 24B for energizing a green light stimulus; the third column, under the letters "Si", includes switches 24C for energizing an auditory stimulus; and the fourth column, under the letters "Sh", includes switches 24D for energizing a tactile stimulus.

The system also includes a block 30 which represents means for programming the response(s) desired from a subject in each test in response to the stimulus or stimuli presented in each test. The block 30 includes rows and columns of circles which represent push-button switches 34 (A to E), with the switches in the first row representing the first test, the switches in the second row representing the second test, etc. The columns of switches represent, in order from left to right, right hand (RH) response, left hand (LH) response, right foot (RF) response, left foot (LF) response, and mouth (M) response.

Referring to the stimulus programmer 20, each row of switches representing a separate test is coupled to a sequencing circuit 40, and a start switch 47 for initiating a series of tests is coupled, both to the sequencing circuit 40 and, through a time delay 49, to a timing clock 50 which is an accurate counter for measuring elapsed time. The system of the invention also includes a separate switch means 60 for each response to be operated by the subject or patient and including separate switches (60A to 60E) for operation by the right hand (RH), the left hand (LH), the right foot (RF), the left foot (LF), and the mouth (M). Other switches may also be added to the system for other responses, if desired.

The switches 34 in the response programmer 30 and the subject response switches 60 are coupled into a response comparator 70, which may be a group of AND gates, in which, for each test, the programmed responses and the given responses are compared. The comparator 70 has outputs 80 to an incorrect response detector 90 and to a printer 100, and the comparator detects failure of the subject response to match the programmed response, and this error is recorded in the printer. The error may also operate an audible signal source 122.

The comparator 70 also has outputs 110 to a circuit 120 which detects premature response of a subject before a test is administered, and this action is also recorded by the printer 100 and sound source 122. This is detected by the subject giving a response before the clock 50 is started, due to the operation of the delay 49 which is inserted between the start switch 47 and the clock.

The comparator 70 also has outputs 130 to a circuit 140 in which entry is made after each test, when the response and program match. This is known as "an all responses satisfied" circuit.

The comparator also has outputs 150 for each subject response switch to lock an information storing latch 160 when each test is responded to. The output of the clock 50 is also coupled to the latches 160, and the elapsed time is locked therein when the subject operates the response switch correctly. This elapsed time is also coupled to the printer 100 which provides a permanent record of the time elapsed for the response to each test.

Suitable reset circuits 170 are provided for resetting all elements of the system at the end of each test and at any other time as desired.

The system 20 shown in FIG. 1 operates as follows. The desired stimuli to be presented to a subject in each test are set into the program by depressing the appropriate switches 24 in block 20. For example, if a red light is to be shown in the first test, the red light switch 24A is closed in the series of switches for the first test; if a green light is to be shown in the second test, the green light switch 24B is closed in the series of switches for the second test; etc. In each test, more than one stimulus can be programmed, if desired. In addition, similarly, the desired responses for each test are set into the response programmer block 30 by closing the appropriate switches 34, and instruction cards are shown to the subject which specify the response he is to make to each test. The programmed responses entered and the instructions given to the subject might be that, if a red light appears in the first test, he respond with his right hand and close the switch 60A provided for the right hand; if a green light appears in the second test, he respond by closing the switch 60D with his left foot; or, in each test, the correct response might be closing switches with both hands or both feet, or the mouth. Thus, it can be seen that a wide variety of stimuli and a wide variety of responses can be programmed to determine whether a patient has problems worthy of further investigation.

Figure 2:
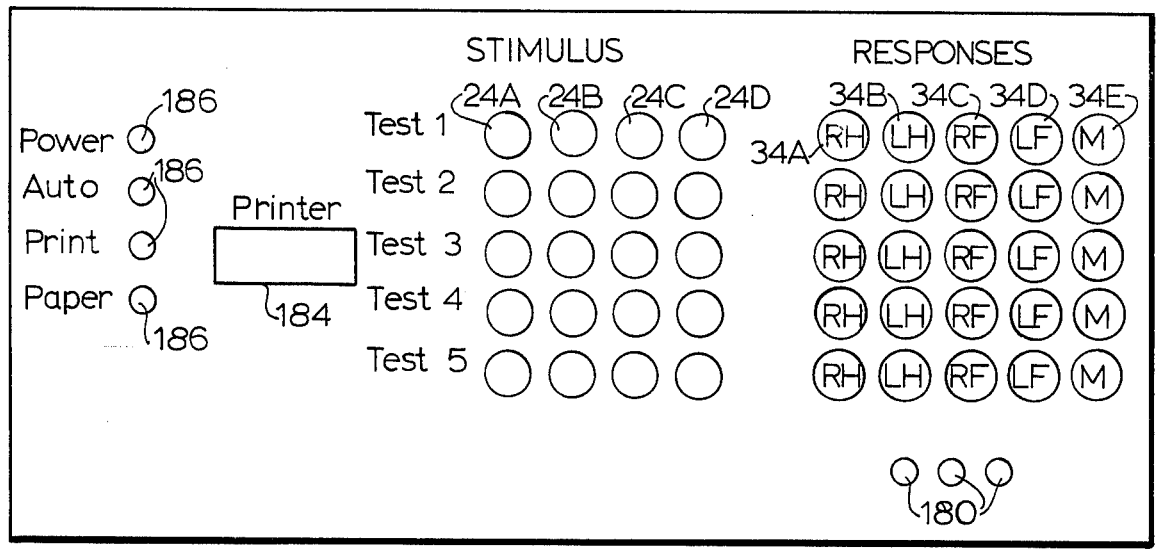
FIG. 2 is an elevational view of the rear panel, the operator's panel, of apparatus embodying the invention.
Figure 3:
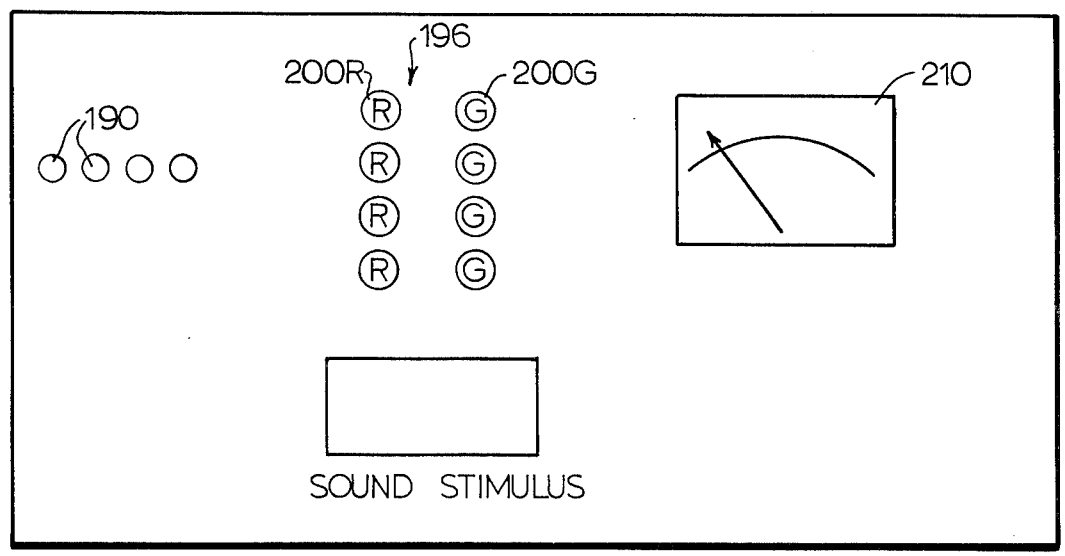
FIG. 3 is an elevational view of the front panel, the subject's panel, of the apparatus of the invention.

In one suitable arrangement, the apparatus of the invention is embodied in a cabinet or housing which includes a rear panel, illustrated in FIG. 2, which is operated by the doctor or technician, and the subject is stationed facing the front panel, shown in FIG. 3. The rear panel carries the arrays of stimulus switches 24 and the response switches 34, disposed side by side. In addition, on the rear panel are provided adjusting knobs 180 to control the intensity, frequency, and pitch of the siren, and adjusting knobs for controlling the intensity of the electric shock. The printer paper outlet 184 and other control knobs 186 are also provided on the rear panel.

The front panel (FIG. 3) carries jacks 190, into which leads to the subject response switches are inserted, an array of red and green lights 200R and 200G which are the stimuli, and a meter 210 on which the subject can view his response. If desired, only one red light 200R and one green light 200G, or a single light which can emit both colors may be used.

Figure 4A:
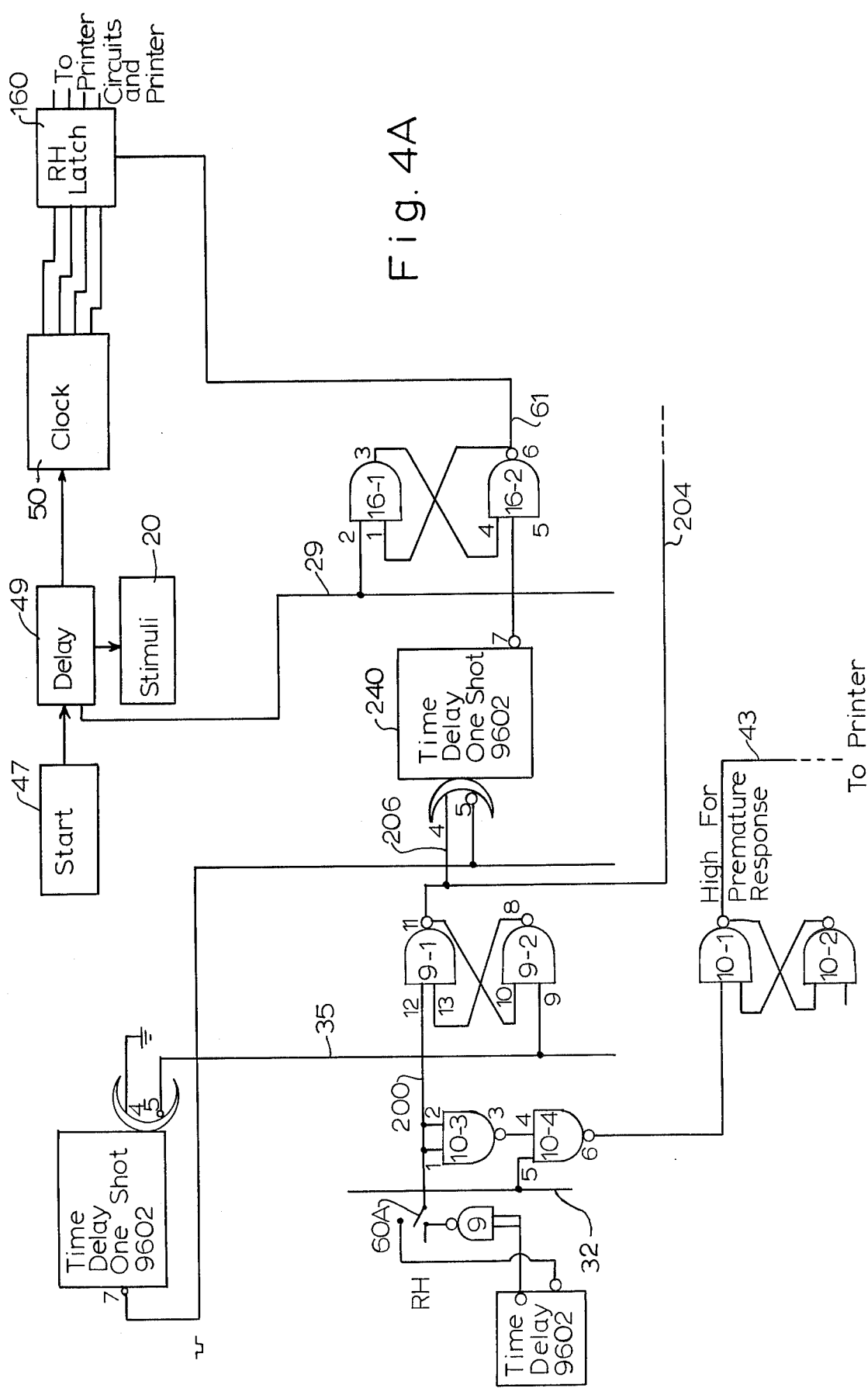
FIG. 4A is a more detailed schematic representation of a portion of the system of FIG. 1.
Figure 4B:
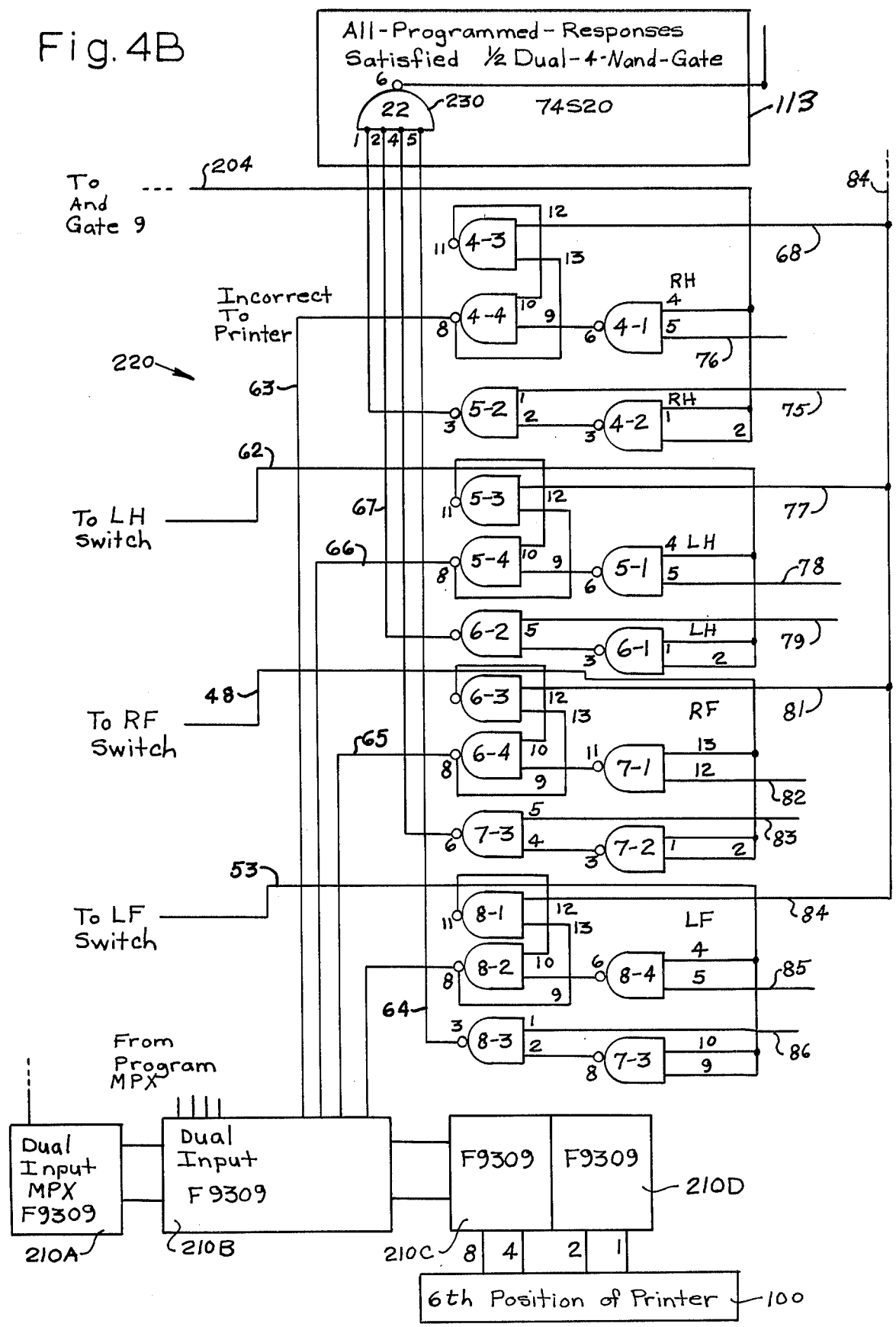
FIG. 4B is also a more detailed schematic representation of a portion of the system of FIG. 1.

A portion of the system of the invention is shown in greater detail in FIGS. 4A and 4B wherein a subject-response switch, e.g., the right hand switch 60A, is connected by a lead 200 to both inputs of an AND gate 10-3, the output of which is connected to one input of an AND gate 10-4. The other input of the AND gate 10-4 is coupled by a lead 32 to the clock operating portion of the system shown in detail in FIG. 5B. The output of the gate 10-4 is coupled to one input of an AND gate 10-1, the output of which is coupled through a series of dual input multiplexers 210 to the printer 100. The multiplexers process binary signals into a form which is usable to drive the printer. The lead 200 is also connected to one input of an AND gate 9-1, the output of which is connected through an AND gate arrangement, including AND gates 4 to 8 (FIG. 4B), to an all-responses-satisfied circuit 230 which is also an AND gate.

The output of the gate 9-1 is also coupled to a 9602 one-shot module 240, the output of which is coupled through AND gates 16-1 and 16-2 to the right hand latch. The outputs of the clock 50 are coupled to the latch, and the outputs of the latch are also coupled through suitable decoding circuitry to the printer.

The circuit of FIGS. 4A and 4B operates in such a way that, when the right hand response switch 60A is closed properly, potentials are coupled through AND gates 9 and lead 204 and the AND gate array 220 to enter the master AND gate 230. Potentials are also coupled through AND gates 9 and lead 206 to one-shot 240 and AND gates 16 to lock the latch 160 in which the elapsed time has been entered and from which the elapsed time information is coupled to the printer.

If the subject response switch is closed prematurely, that is, before the clock is started, potentials are coupled through gates 10 to the dual input multiplexer chain and to the printer to record that fact therein, preferably by a red printout.

If closure of a switch represents an incorrect response, that is, the response does not match the program, a potential appears at the appropriate "8" gate output in array 220, and this is suitably coupled to the printer and represented by a "1" preceding a time.

A more detailed system for practicing the invention is illustrated, mostly in block form, in FIGS. 5A to 5I. To simplify the drawing, some circuit elements, such as power supplies, resistors, grounds, etc., are omitted since they can be readily provided by those skilled in the art.

Figure 5A:
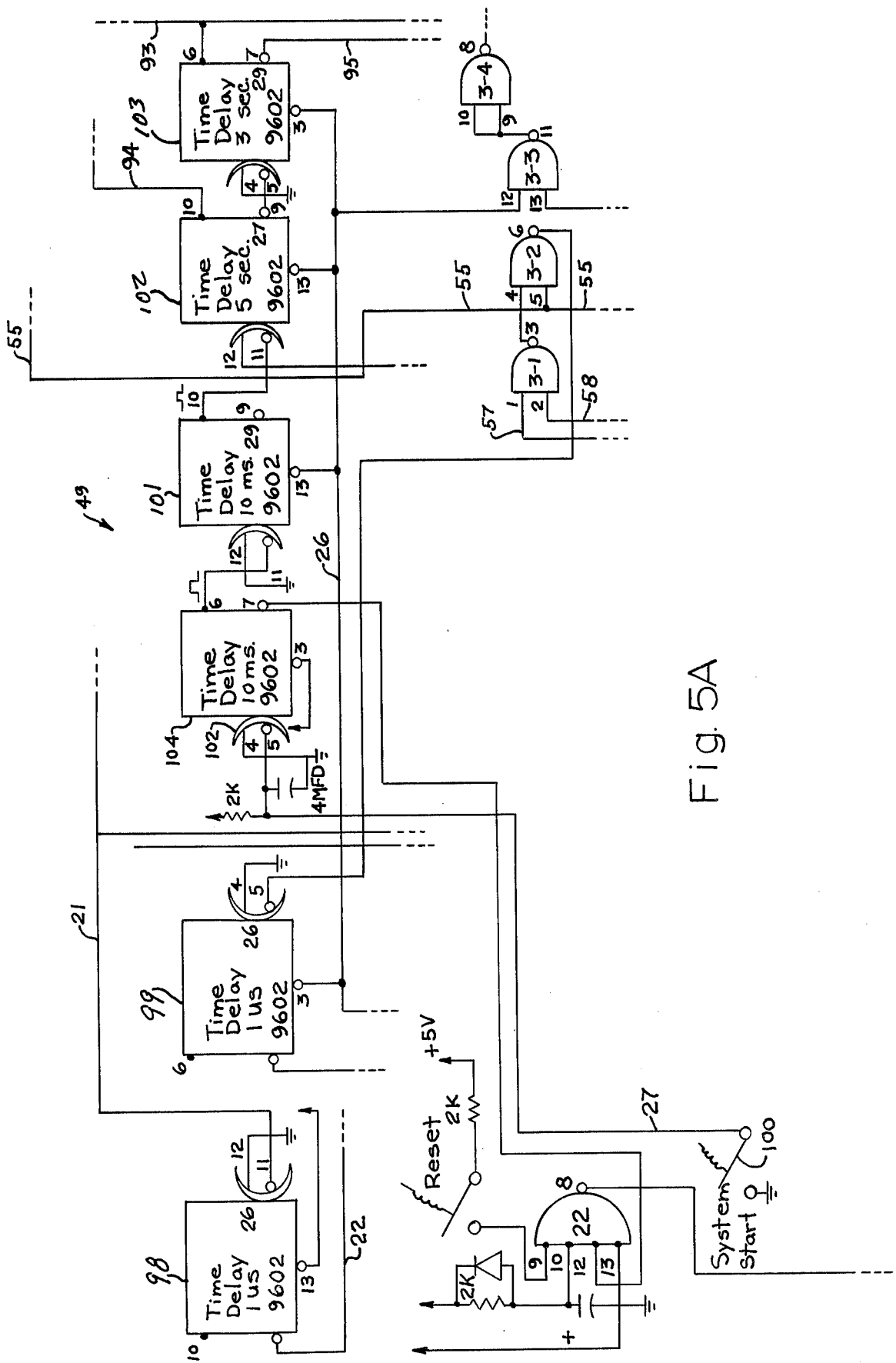
FIGS. 5A to 5I are more detailed schematic representations of electronic apparatus for practicing the invention.
Figure 5B:
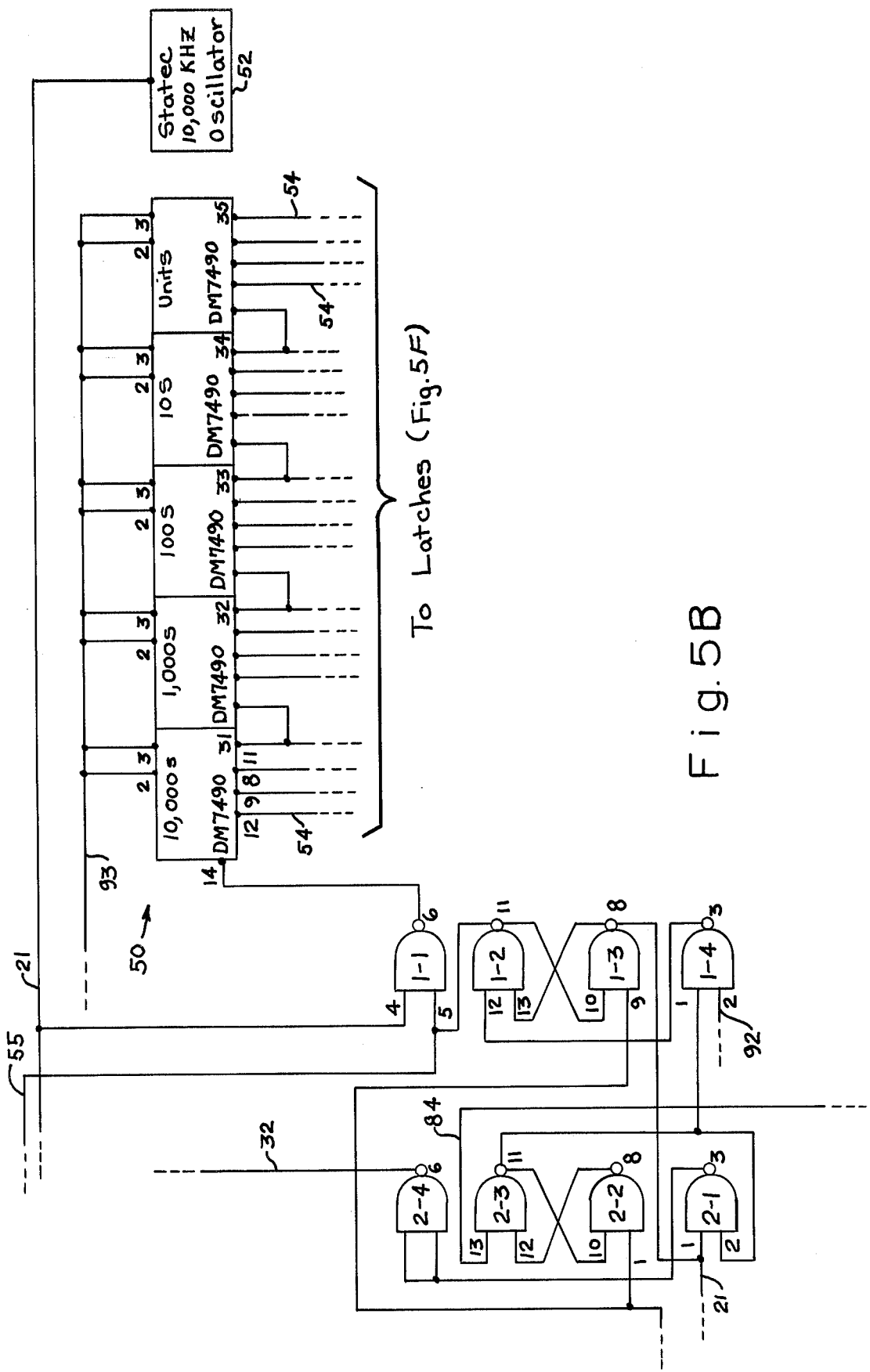
Figure 5C:
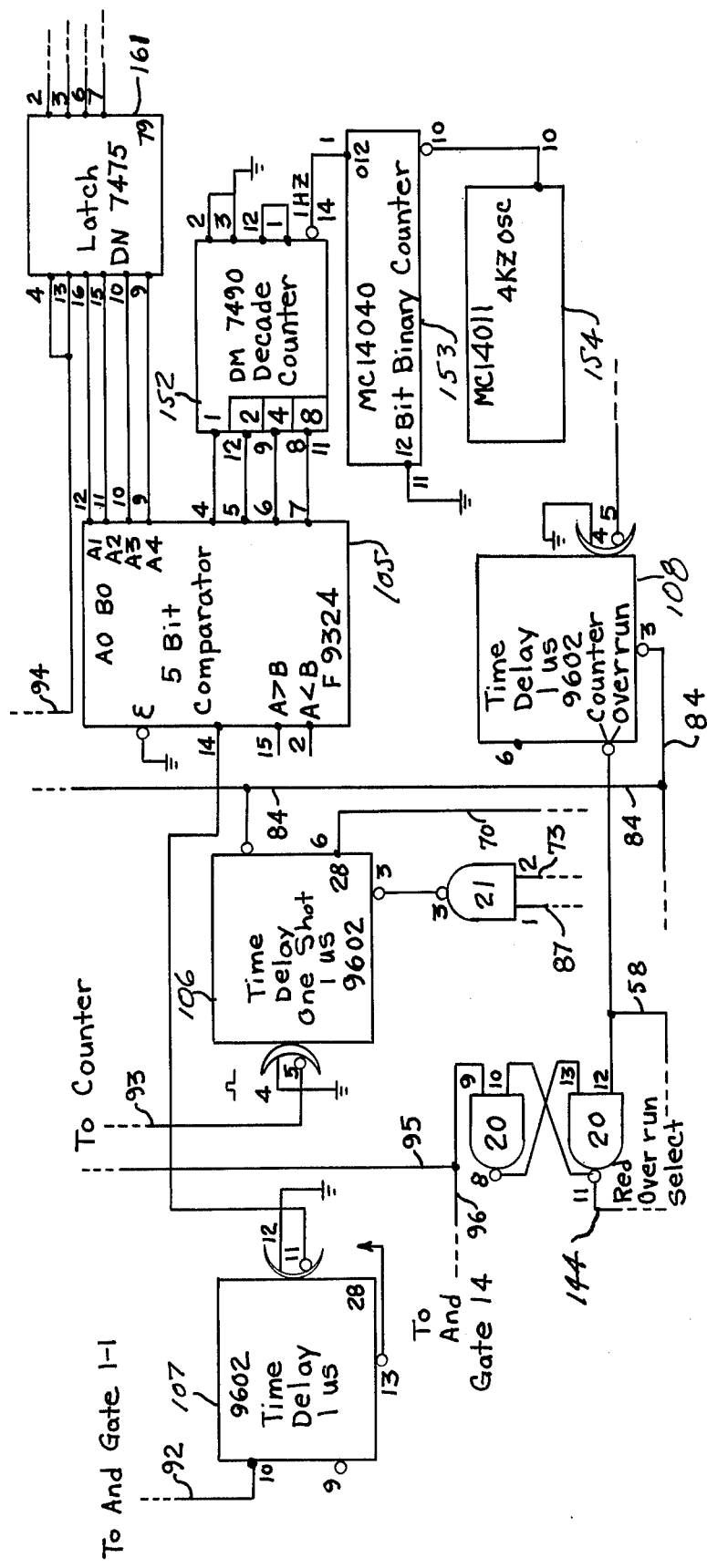

The system includes the clock 50 (FIG. 5B), which is an extremely accurate counter for counting to ten-thousandths of a second, the counter being driven by a 10,000 KHz oscillator 52. Time delay circuit 49 is made up of a series of time delay modules which control the operation of the oscillator 52. The time delays may be 9602 modules. The clock 50 has leads 54 to the latches 160 (FIG. 5F), and the latches have leads 56 to the printer control circuitry (FIGS. 5F and 5G). FIG. 5E shows the stimulus programming switches 24 for the lights and siren coupled through 9312 multiplexers and to drivers 162, 163 and 164 for the stimuli. The connections to the time delay circuit and the AND gates 4 to 8 are also shown in FIGS. 5A and 5B.

The other circuit modules shown are used to perform various timing and control functions.

In the embodiment of the invention shown in FIGS. 5A to 5I, the circuit modules used were as follows:

1. The 4-input multiplexers were selected from National Semiconductor series DM 9309/DM 8309 modules.

2. The multivibrators were selected from National Semiconductor DM9601/DM8601 modules and Signetics S9702/N9602 modules.

3. The latches were selected from National Semiconductor SN5474/SN7475 modules.

4. The counters were selected from National Semiconductor Series 54/74 modules.

5. The 8-input multiplexers were selected from National Semiconductor DM9312/DM8312 modules.

Other comparable modules could be used.

The subject invention comprises a biomedical instrument for measuring the alertness of an individual. It is a solid state electronic device conceived to measure the cerebro-neuro-electrical responsiveness of the visual, auditory and tactile sensory stimuli of man to respective stimuli with an accuracy of 0.0001 second. The sensitivity involved exceeds that usually physiologically required by a factor of 100. To illustrate this sensitivity, one need only to place 15 drops of ethyl alcohol (cognac, if preferred) under the tongue and, within 15-30 seconds, a delay in response will result and is recorded and can be compared with that individual's norm. The majority of subjects thus far tested range from 15-20 years of age. This alcohol-based delay at this minimal amount of absorption appears in hundredths of a second.

The auditory and visual apparatus involve a finger (usually index) of both hands and both shod feet that are appropriately adjusted on specially constructed pads for maximum accuracy. This will be described with reference to FIGS. 8 and 9. The visual stimuli are either red or green solid state lights concentrically arranged to about the size of a five-cent piece, for maximum effectiveness at 25-30 cm, the usual reading distance. The auditory stimulus is a small device on the front panel facing the individual that simulates an ambulance or police siren and whose volume and pitch can be regulated. The tactile stimulus consists of applying a small harmless electric shock, which is easily controlled for comfort by the individual; any portion of the body can be tested. The patient responds by breaking or completing the circuit inside a plastic wedge held between the teeth, and this, of course, immediately registers on the panel, as well as on the printer tape. A suitable mouth switch is shown in FIG. 6.

Any errors, such as premature or wrong anatomical responses, besides being recorded on tape, are also answered audibly by a signal.

As noted above, there are five test runs which are pre-programmed in any desired combination. The subject responds to the instructions, which may be on printed cards, either by pressing a switch to the closed position or breaking a switch circuit through raising the finger from the contacted pole terminal (FIG. 8 and 9) resting on a table. Errors, such as premature reaction or the wrong hand or foot, appear immediately on the tape, properly identified, for example by an accompanying numeral one. If the reaction time is over 10 seconds, all results appear in red. The test can be interrupted at any time, rerun, or altered as desired.

Figure 5D:
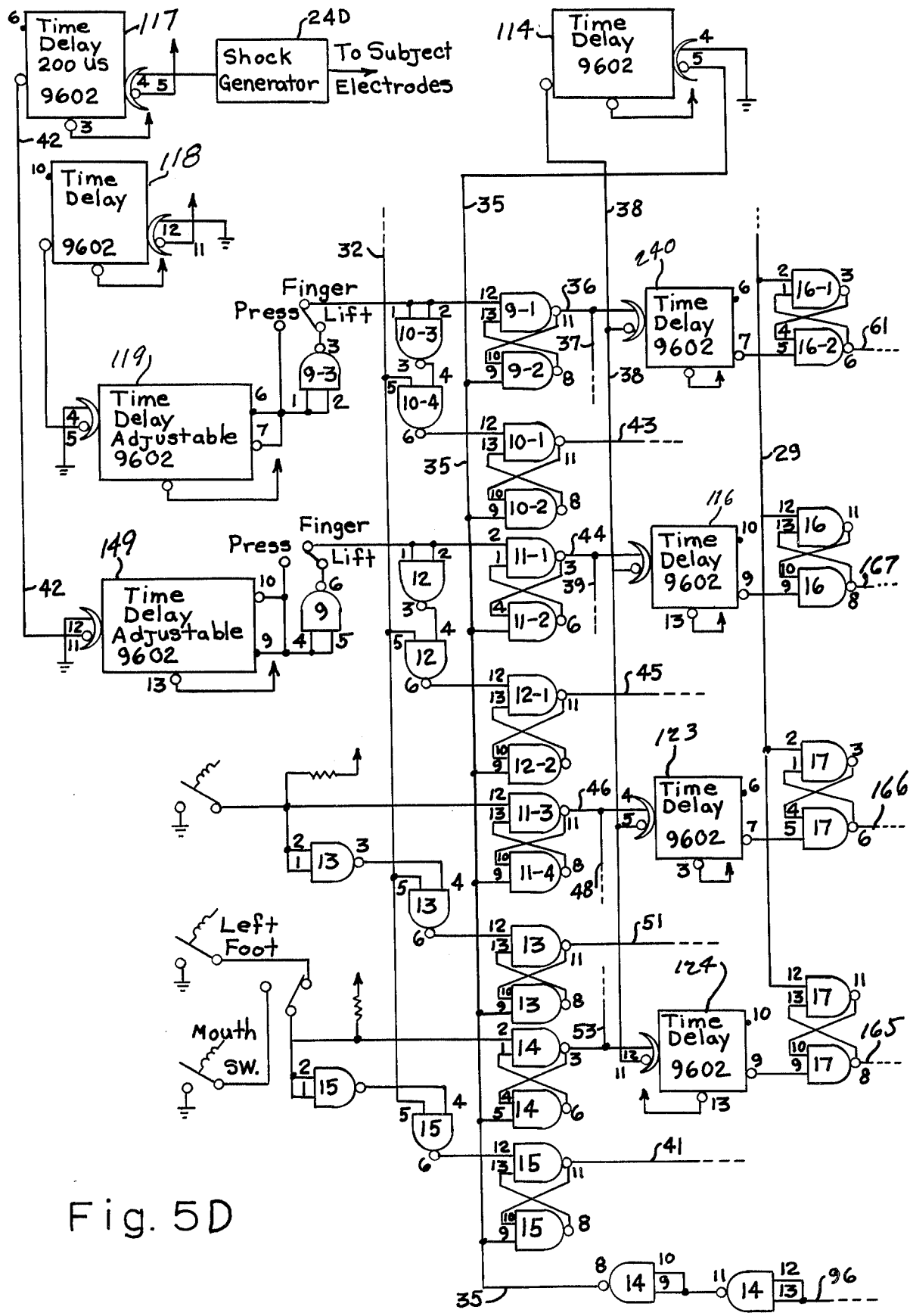
Figure 5E:
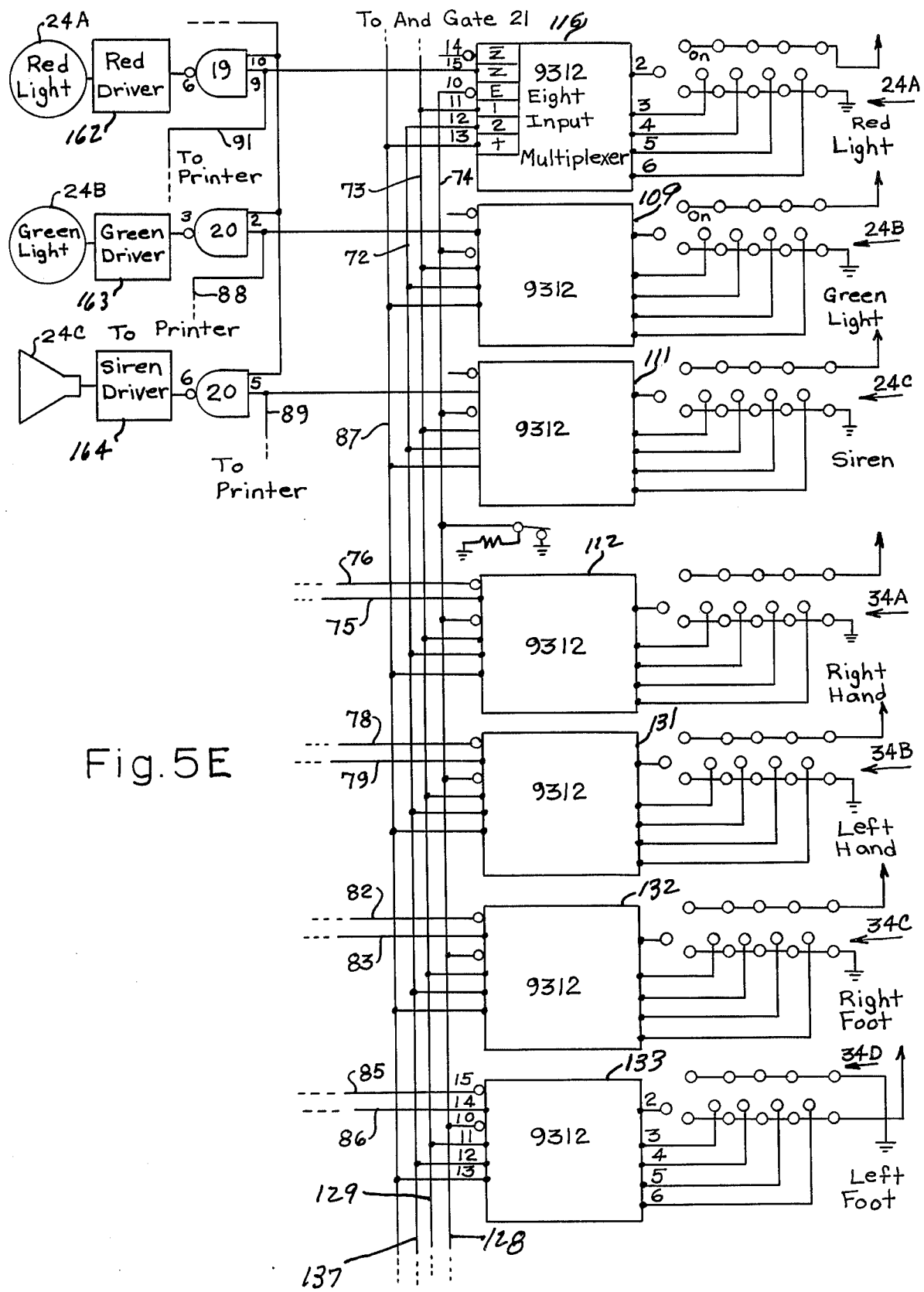
Figure 5F:
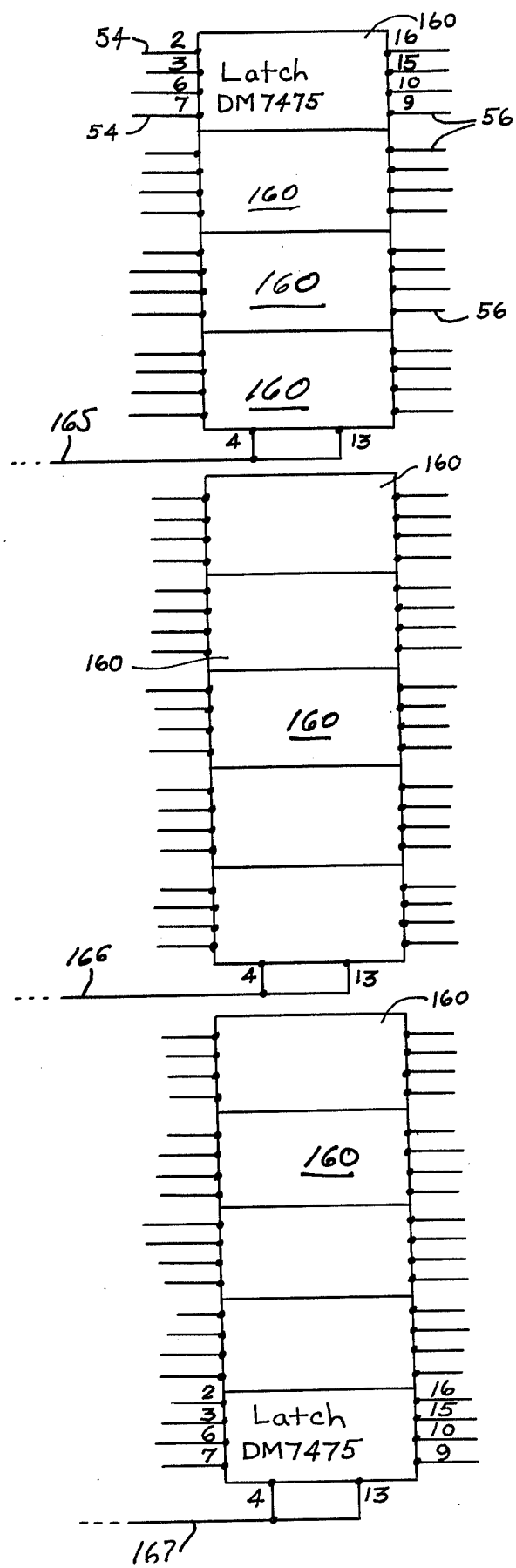
Figure 5G:
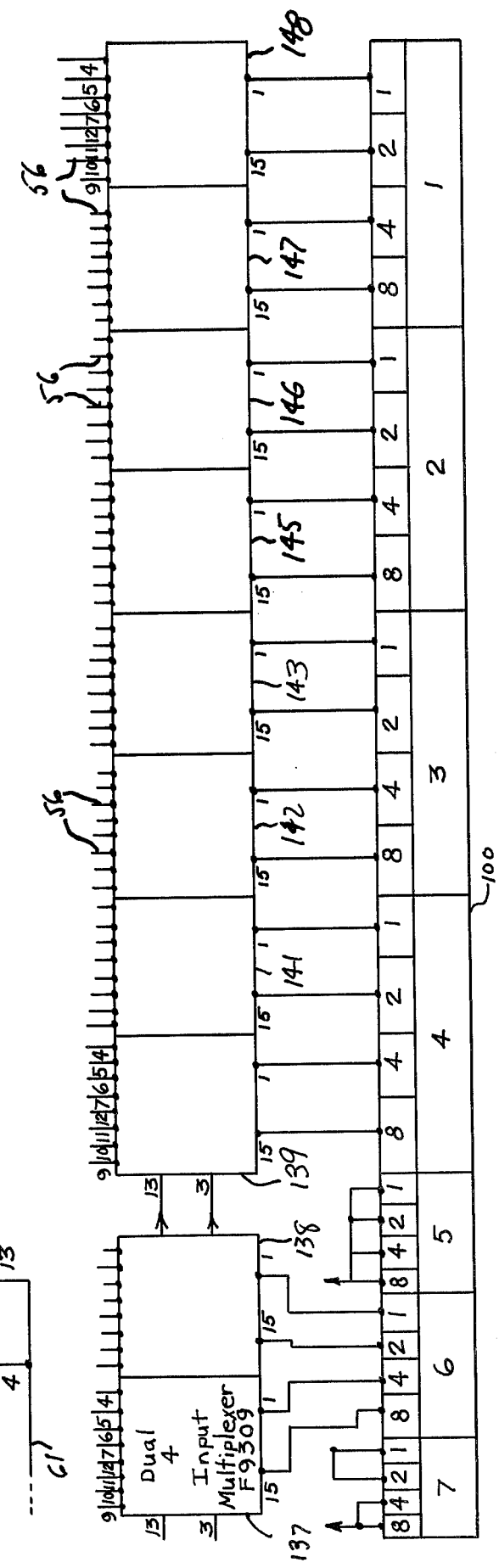
Figure 5G:
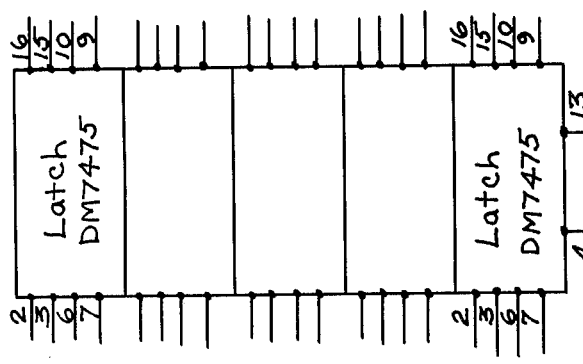
Figure 5H:
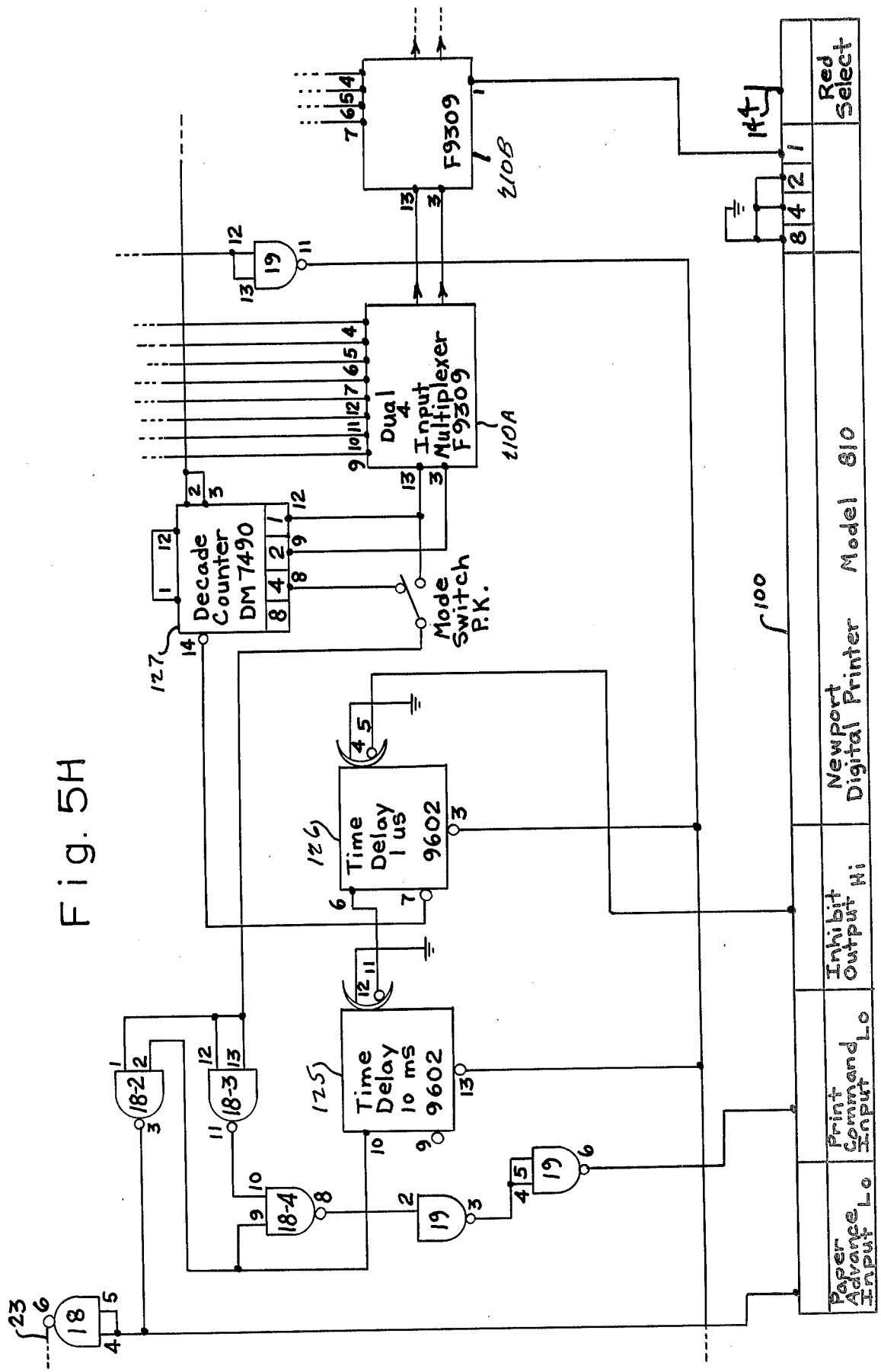
Figure 5I:
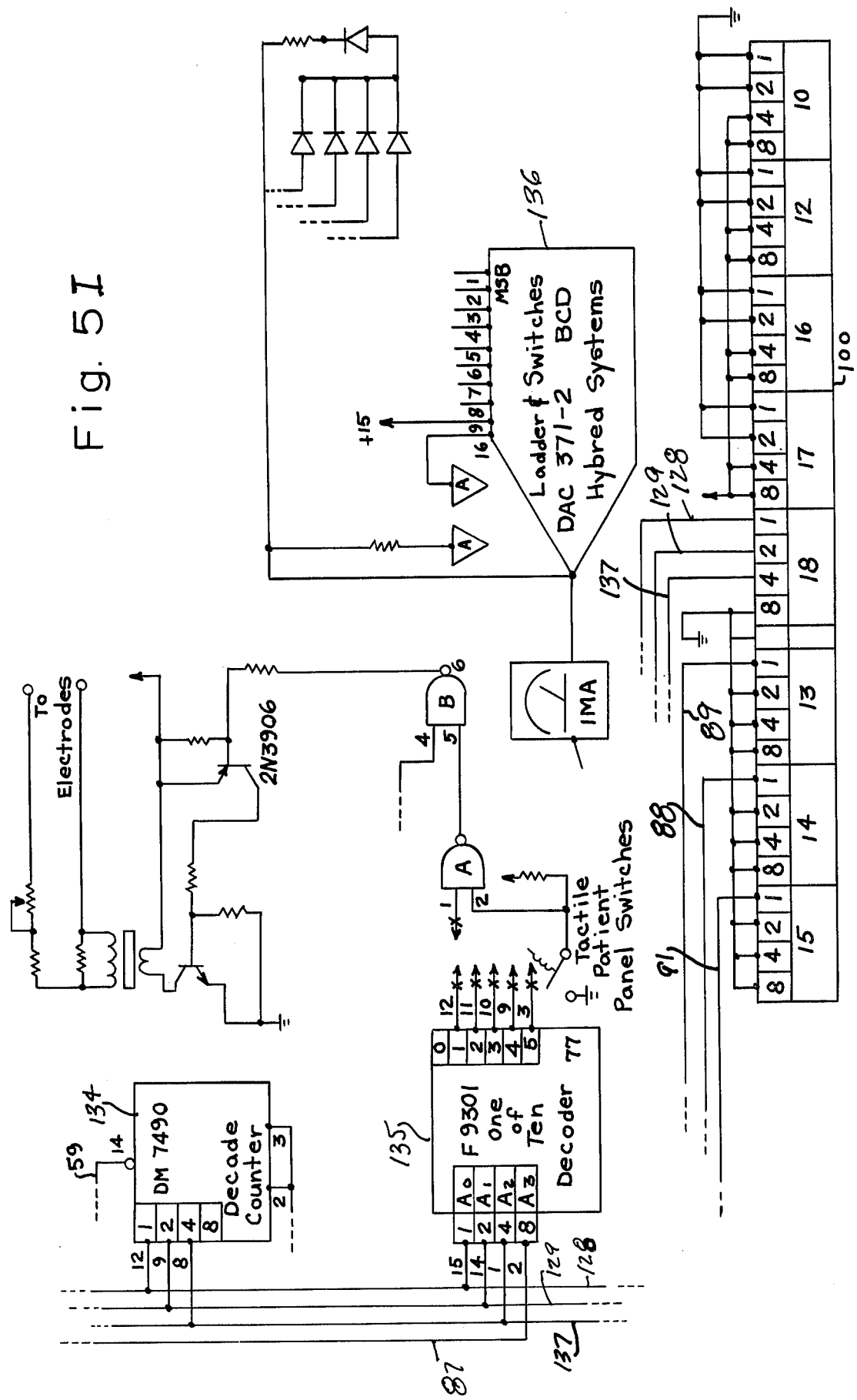

FIG. 6 shows a cervical halter 500 for a mouth switch 501 corresponding to the mouth switch shown in the lower left-hand portion of FIG. 5D. The mouth switch 501 is a device of the response means and serves to furnish indications (namely, electric signals) as a result of relative movement of a subject's jaws on application of a stimulus, particularly a tactile stimulus in the form of an electric shock. The operation of the mouth switch 501 is based on the principle that a shock (e.g., fright, pain or surprise) invariably results in opening of the mouth, i.e., in a change of relative position of the subject's jaws. If desired, the patient can be instructed to close the mouth and to thereby complete the circuit instead of breaking the circuit. The illustrated switch 501 comprises two externally serrated portions 502, 503 which are insertable between the upper and lower rows of teeth of a subject. The portion 502 (which may be elastic) is biased away from the portion 503 by a helical spring 504 and carries an adjustable screw 505 whose shank can depress the mobile contact 507 of a microswitch 506. The latter is connected to a separable coupling 508 on an arm 509 of the halter 500 by a cable 510. A further cable 511 connects the coupling 508 to one of the jacks 190 shown in FIG. 3. The cervical halter 500 is optional; it can be replaced by a simple clip for attachment of the switch 501 to an article of apparel of the subject, e.g., in a manner known from the art of microphones.

Tactile stimuli are preferably delivered in the form of harmless electric shocks whose intensity can be selected by the test subject. The poles of the shock applying means can be applied to selected portions of the body of a subject by conventional Velco straps or the like. One such strap is shown in FIG. 7, as at 520. It carries one or more grounded contacts 521 to cutis and a second contact 522. A cable 523 connects the contacts to the corresponding portion of the circuitry in or on the housing of the apparatus. The latter is preferably furnished with several shock applying means, e.g., one for each extremity, one for the head and one for the trunk of a subject.

The portions 502, 503 of the switch 501 are held (gently but firmly) between the jaws of a subject under test and the subject automatically permits the spring 504 to move the portions 502, 503 apart in response to administration of a shock. The portions 502, 503 preferably consist of a lightweight plastic material which can be readily cleaned and sterilized after each use. The arrangement may be such that opening of the jaws (i.e., a movement of portions 502, 503) results in opening or closing of the microswitch 506. In either event, the device 501 furnishes an indication as soon as the subject reacts to the application of a stimulus. Opening of the jaws may be voluntary or involuntary, depending on the nature and intensity of the applied stimulus or stimuli. As a rule, the subject will be instructed to respond, as quickly as possible, to all visual, auditory or tactile stimuli. It has been found that the switch 501 enables a subject to react to stimuli within surprisingly short intervals of time.

The microswitch 506 can be replaced with a photoelectric cell or with any other component which is capable of furnishing electric signals or other indications in response to minute changes in the relative positions of portions 502, 503.

The response means for operation by the extremities of a subject under test may include transducers of the type shown in FIGS. 8 and 9. The illustrated transducer 530 is designed to be operated by the index finger of a hand. The finger is properly flexed (as shown in FIG. 8) while the elbow of the same hand rests on a suitable support. The distance which the finger must cover in order to furnish an indication is preferably a small fraction of one millimeter (e.g., 0.5856 mm which is the thickness of a conventional razor blade). The light source of the transducer 530 is a solid state lamp 531 shown in FIG. 9. This lamp is installed in a casing 532 at one side of a plastic light intercepting block 533 opposite a solid state photocell 534. The block 533 intercepts the major part of the solid state light save for a narrow band having a height which is a fraction of one millimeter. The recess 535 of the casing 532 is suitably contoured for insertion of a finger, and the casing 532 further comprises a finger stop 536. An adjusting screw 537 in the top wall of the casing 532 can be rotated to move the inserted portion of the finger to a desired position immediately above the band of the solid state light adjacent the polished upper side of the block 533. The base 538 of the casing 532 is provided with a friction pad 539. Slight scattering of the light due to molecular unevenness of the smooth upper side of the block 533 compounds the efficiency of the transducer. The signal which is furnished by the photocell 534 is amplified for the printer 184 and for a lamp 540 which indicates the position of the finger in the recess 535.

Prior to start of a test, the screw 537 is manipulated to insure that the inserted finger does not interfere with travel of light from the lamp 531 to the photocell 534. The lamp 540 on the casing 532 is turned on or off when the finger assumes the optimum position.

The construction of transducers which are actuated by the (preferably lightly shod) feet of the subject is preferably analogous.

The transducer 530 of FIGS. 8 and 9 is effective in two ways. Thus, it can interrupt the narrow band of solid state light in response to downward motion of the finger, or it can permit solid state light to reach the photocell 534 in response to upward movement of the finger in the recess 535. Thus, when properly inserted, the finger can rest on the block 533 or it can abut against the plate 541 at the lower end of the adjusting means 537. The pinions of the finger or fingers involved are preferably the phalangeal metacarpal joint and, to a lesser extent, the proximal interphalangeal joint. A lock nut 542 can be provided to fix the adjusting screw 537 in a selected optimum position.

The width of reactive space which is needed to turn the system on or off in response to upward or downward movement of the finger need not exceed 0.25 mm.

The applications of the apparatus are numerous, and some presently preferred applications include:

1. Evaluation of the degree of cerebral arteriosclerosis (senility).
2. Drug, pharmaceutical preparations:
   A. Abuse, whether accidental or willful.
   B. Calibration of dosage and establishing safety levels, e.g., to study untoward effects, such as dizziness, insomnia, drowsiness, sleepiness and/or overstimulation.
   C. Testing new pharmaceuticals.
   D. Drug tolerance.
3. Alcohol and nicotine effects in reference to automobile driving, flying, sports participation or other activity which is dependent on speed, timing and precision performance.
4. Insurance purposes, effects of environmental pollution, inspiratory and/or digestive.
5. Selection of individuals for special sensitive occupations, such as political or military intelligence; effects of mental or emotional conflicts (prisoners of war, espionage agents).
6. A primary disorder of the brain and/or spinal tract, e.g., neoplasms, traumatic lesions, congenital abnormalities, inflammatory conditions, toxic reactions.
7. Metabolic and endocrine disorders, e.g., electrolyte imbalance, gout, hypoglycemia, diabetes mellitus, hyper- and hypothyroid states, etc.
8. Nutritional deficiencies.
9. Other areas of clinical investigations, e.g., hypervitaminosis, hyperproteinemia, certain genetic disorders including inborn errors of metabolism or acquired deficiencies.
10. Alcoholism and related nosology.
11. Anxiety, depression and other neuropsychiatric disorders with evaluation and control of drug administration.
12. Establishing criteria, on an individual basis, for employment, insurance and/or retirement purposes.
13. Detection of harmful neurological effects caused by environmental toxins and contaminants introduced into the body through inhalation or digestion, or through the skin by noxious gases, or by ionizing or non-ionizing radiation.

14. Mental retardation.

15. Inborn dexterity including measurement of potential limb ambidexterity and determination of right or left hand and foot predominance.

16. Studies of twins and other multiple births.

17. Degree of extremity impairment and rehabilitation in paralysis or paresis with cerebro-spino-neuromuscular pathology due to muscular dystrophy, muscular atrophy, multiple sclerosis, post syncope, trauma, microbial, viral or toxic states, oncosis, congenital or developmental abnormalities, cerebral atropy and other causes.

18. Other behavioral investigations of activity of brain and associated systems.

Without further analysis, the foregoing will so fully reveal the gist of the present invention that others can, by applying current knowledge, readialy adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the claims.

What is claimed is:

1. Apparatus for testing human responses to stimuli, comprising
   (a) a plurality of stimuli including tactile stimuli;
   (b) means for selecting and setting into program each of said stimuli;
   (c) response means for operation by a subject under test, including a device arranged to furnish indications as a result of relative movement of the jaws of a subject under test on application of a stimulus;
   (d) a clock coupled to said stimuli and to said response means for registering the time which elapses after the start of a test and the operation of a stimulus for the subject to provide a response; and
   (e) means for controlling and interrelating the operation of said stimuli, said response means and said clock.

2. Apparatus as defined in claim 1, further comprising time delay means coupled to said clock for delaying the start of the running of said clock for a predetermined interval of time after a test is initiated.

3. Apparatus as defined in claim 1, wherein said tactile stimuli include a source of electric shock and said stimuli further include a plurality of lights of different colors, means for energizing said lights in different combinations and sequences, a source of sound, and means for varying the pitch, frequency and/or intensity of sound.

4. Apparatus as defined in claim 1, further comprising means for detecting the operation of said response means, before the operation of said clock is initiated, to represent a premature response.

5. Apparatus as defined in claim 1 for testing human responses to various stimuli, wherein said stimuli form several groups one of which includes said tactile stimuli, another of which includes visual stimuli and a further of which includes auditory stimuli, said response means further including at least one additional device operable by a subject under test to furnish indications on application of a stimulus.

6. Apparatus as defined in claim 5, wherein each group of stimuli constitutes a test unit, and further comprising switch means for setting selected stimuli in each group into a test.

7. Apparatus as defined in claim 6, further comprising sequencing means for energizing each group of selected stimuli in turn to present a plurality of tests of a subject.

8. Apparatus as defined in claim 5, further comprising sequencing means for sequentially energizing the stimuli which are programmed to be operated during each of a series of tests.

9. Apparatus as defined in claim 8, further comprising comparator means for receiving the programmed responses and the exercised responses in each test, and means responsive to the output of said comparator means for registering a correct response or an incorrect response to each test.

10. Apparatus as defined in claim 5, further comprising means for storing the time of response for each test and utilization means coupled to said storing means for representing a time unit stored in said storing means.

11. Apparatus as defined in claim 10, wherein said storing means includes a plurality of latches, each latch being arranged to store a time unit generated by said clock.

12. Apparatus as defined in claim 11, further comprising a response comparator and means for coupling said latches to said response comparator.

13. Apparatus as defined in claim 5, wherein said visual stimuli include a red light and a green light, said auditory stimuli including a siren.

14. Apparatus as defined in claim 5, further comprising a switch for each stimulus whereby the stimulus can be entered into a test program.

15. Apparatus as defined in claim 5, further comprising means for detecting the operation of said response means before the operation of said clock is initiated to represent a premature response, and a printer having means for providing a printout denoting said premature response.

16. Apparatus as defined in claim 1, further comprising means for detecting the expiration of a predetermined maximum period of time before a subject responds to a test.

17. Apparatus as defined in claim 1, wherein said device includes a pair of relatively movable portions insertable between the teeth of a subject, means for biasing said portions apart, and means for generating indications on movement of said portions in response to relaxation of tooth pressure upon said portions.

18. Apparatus as defined in claim 17, wherein said indications generating means includes a microswitch.

19. Apparatus as defined in claim 1, wherein said response means further includes a transducer actuatable by a portion of an extremity of a subject under test.

20. Apparatus as defined in claim 19, wherein said transducer includes a source of radiation, a photocell in the path of radiation issuing from said source, means for partially intercepting radiation intermediate said source and said cell, and a casing for confinement of said portion of an extremity in such position that a movement of said portion of an extremity results in interception of radiation which is not intercepted by said intercepting means.

21. Apparatus as defined in claim 20, wherein the height of radiation which is not intercepted by said intercepting means is a fraction of one millimeter.

22. Apparatus for testing human responses to various stimuli, comprising
   (a) a housing having a first wall facing a subject to be tested and a second wall facing the operator;

(b) a plurality of visual stimuli disposed on said first wall;
(c) a source of an auditory stimuli mounted on said first wall;
(d) a source of a tactile stimulus mounted on said front wall;
(e) response indicating means operated by a subject, including a device arranged to furnish indications as a result of separation or closure of the jaws of a subject on application of a stimulus, particularly a tactile stimulus;
(f) receptacles on said first wall;
(g) means for coupling said response indicating means to said receptacles;
(h) electronic circuitry provided in said housing to control and operate said stimuli and said response indicating means;
(i) means for programming said stimuli and the desired responses, said programming means being provided on said second wall; and
(j) means for coupling said programming means to said circuitry.

* * * * *